United States Patent
Lu et al.

(10) Patent No.: US 10,231,625 B2
(45) Date of Patent: Mar. 19, 2019

(54) INTERNALLY-ADMINISTERED RADIATION THERAPY USING ENDOSCOPIC IMAGE GUIDANCE

(71) Applicants: OHIO STATE INNOVATION FOUNDATION, Columbus, OH (US); Zhilin Hu, Cleveland, OH (US)

(72) Inventors: Lanchun Lu, Powell, OH (US); Zhilin Hu, Cleveland, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 162 days.

(21) Appl. No.: 15/059,176

(22) Filed: Mar. 2, 2016

(65) Prior Publication Data

US 2016/0263401 A1    Sep. 15, 2016

Related U.S. Application Data

(60) Provisional application No. 62/131,959, filed on Mar. 12, 2015.

(51) Int. Cl.
*A61N 5/10* (2006.01)
*A61B 5/00* (2006.01)
*A61B 8/12* (2006.01)

(52) U.S. Cl.
CPC .......... *A61B 5/0066* (2013.01); *A61N 5/1007* (2013.01); *A61N 5/1049* (2013.01);
(Continued)

(58) Field of Classification Search
CPC .......... A61N 5/1002; A61N 2005/1003; A61N 2005/1005
(Continued)

(56) References Cited

U.S. PATENT DOCUMENTS 7,163,504 B1 * 1/2007 Chiu .................. A61M 25/1011
                                                                600/3
7,289,842 B2 * 10/2007 Maschke .............. A61B 5/0066
                                                                600/466
(Continued)

OTHER PUBLICATIONS

Isenberg et al., "In vivo imaging of the biliary (BD) and pancreatic duct (PD) with Optical Coherence Tomography (OCT) during ERCP accurately identifies dysplastic cellular changes," Gastrointestinal Endoscopy 67, AB 107 (2008).
(Continued)

*Primary Examiner* — Samuel Gilbert
(74) *Attorney, Agent, or Firm* — Michael Best & Friedrich LLP (57) ABSTRACT

Systems and methods are provided for a catheter-based system of image-guided internally-administered treatment of medical conditions such as, for example, pancreatic cancer. A distal end of a catheter is positioned at a target site inside a patient's body. An imaging probe extended through the catheter collects image data of patient tissue at the target site. The image data is processed and a treatment plan is developed. A radiation source positioned at the distal end of the catheter without removing the catheter. In this way, images collected at the target tissue site can be used to develop a treatment plan and to guide the localized positioning and operation of a treatment device at the same internal tissue site—thereby providing higher resolution imaging than external-based imaging modalities and reduced exposure to radiation as compared to externally applied radiation therapies.

11 Claims, 12 Drawing Sheets

(52) U.S. Cl.
CPC ............... *A61B 5/4836* (2013.01); *A61B 8/12* (2013.01); *A61N 5/103* (2013.01); *A61N 2005/1058* (2013.01); *A61N 2005/1076* (2013.01)

(58) Field of Classification Search
USPC .......................................................... 600/3
See application file for complete search history.

(56) References Cited

U.S. PATENT DOCUMENTS

2003/0135102 A1\* 7/2003 Burdette ................. A61B 8/12
600/407
2007/0135887 A1\* 6/2007 Maschke ................. A61B 8/12
623/1.11

OTHER PUBLICATIONS

Kubo et al., "High Dose-rate brachytherapy treatment delivery: Report of the AAPM Radiation Therapy Committee Task Group No. 59," Medical Physics, vol. 25, No. 4, Apr. 1998, 375-403.

\* cited by examiner

INTERNALLY-ADMINISTERED RADIATION THERAPY USING ENDOSCOPIC IMAGE GUIDANCE

RELATED APPLICATIONS

This application claims the benefit of U.S. Provisional Application No. 62/131,959, filed Mar. 12, 2015 and entitled "INTERNALLY-ADMINISTERED RADIATION THERAPY USING ENDOSCOPIC IMAGE GUIDANCE, the entire contents of which are incorporated herein by reference.

BACKGROUND

The present invention relates to systems and methods for developing treatment plans for conditions such as, for example, cancers and administering treatments accordingly.

SUMMARY

Pancreatic cancers are one of the most lethal cancers. More than 30,000 people in the United States each year are diagnosed with adenocarcinoma of the pancreas. The American Cancer Society estimates that 37,680 cases of pancreatic cancer would be diagnosed in the United States in 2008, with an estimated 34,290 deaths, and the overall 5-year survival rate is only 3% to 5%. By 2015, those numbers have grown to 48,960 diagnosed cases of pancreatic cancer and 40,560 deaths. The median survival duration for untreated advanced cancer of the pancreas is about 3½ months—with good treatment this increases to about six months. About 95% of pancreatic cancer arises from the exocrine portion of the organ which mostly (~90%) are from ductal cells that line the pancreatic ducts. These cancers develop when cancerous cells form in the pancreatic and bile ducts. Pancreatic and bile cancers spread rapidly and are seldom detected in its early stages.

The survival rate can increase to approximately 20% if the tumor is removed completely before the cancer spreads to lymph nodes. However, only 10% of patients are candidates for surgical resection at the time of diagnosis. Even after resection of a seemingly localized neoplasm, long-term survival is poor. Therefore, early detection of cancerous cells is critical to increasing the survival rate. Adjuvant therapy with chemo or chemoradiotherapy has the potential to achieve long-term success in treating this disease. Following surgical resection, patients treated with chemotherapy and radiation therapy (RT) have slightly improved survival as compared to surgery alone. Although external beam radiation therapy appears to improve local control of disease, it has an unacceptable level of toxicity and may cause serious side effects such as duodenal ulcers, which may be due to the unavoidable high dose of radiation delivered to the organs surrounding to the pancreas.

As such, early detection and treatment of tumors is critical to the cancer survival rate and reducing the risk of recurrence. Medical imaging techniques might be implemented to help physicians diagnose cancers and perform computerized treatment planning and simulation for radiation therapy. However, external imaging modalities such as CT, MRI, and PET provide limit resolution and potentially obstructed views of the tissue in question. Therefore, the systems and methods discussed below utilize internally administered endoscopic imaging modalities for early-stage diagnosis of cancers of the esophagus, bronchus, pancreatic, and colorectal cancer. Most of these tumors begin to develop from inner layers of the tissue and then spread into the deeper and outer layers. Although CT and MRI are widely used to diagnose and localize large solid tumors, they are less adequately suited for early-stage detection of smaller, soft-tissue tumors. In general, CT can only detect tumors greater than 1 mm in size and has difficulty imaging soft tissue. MRI has poor spatial resolution compared with CT and it is time consuming to perform and collect imaging.

The most recently developed endoscopic imaging techniques are endoscopic ultrasound (EUS) and endoscopic optical coherence tomography (EOCT). EUS has started to be used in clinics and are being evaluated through clinical trials, while OCT is still primarily at the stage of laboratory research within a few clinical trials. While a conventional endoscopy can only show the inner surface of an aerodigestive organ, EUS and EOCT can be used to generate images of not only the surface, but also the structure deep into the tissue, which is extremely useful for diagnosis of cancers. However, even compared with EUS, OCT has a much better spatial resolution, which can detect a structure as small in size as a few micro-meters. This is very crucial for early detection of cancers. OCT may also have the potential to detect the residual tumor tissues after a surgery, which can lead to Intra-operation radiation therapy (IORT).

Using the systems and methods described herein, the early detection of pancreatic cancers becomes feasible using a high-resolution, non-invasive Optical Coherence Tomography (OCT) device. This non-invasive optical imaging system provides smaller than 10 micrometers spatial resolution and was developed to detect pancreatic cancers at their early stages. The pancreatic and bile endoscopic OCTs have demonstrated that normal and abnormal pancreatic and bile ducts are distinguishable. Clinical trials on patients indicate that the diagnostic successful rate reaches 96%. With this internal imaging modality, combined with other diagnostic modalities such as brushing and biopsy, early diagnosis of pancreaticobiliary cancers is practical and accurate. The OCT image is not only better in the early detection of cancer but can also provide the accurate position of the tumors—leading to more precise radiation treatment.

The systems and methods described herein provide a new technique to detect pancreatic cancer and to treat it at early stages, such as Intraductal Papillary Mucinous Neoplasms of the Pancreas (IPMNs). These systems and methods detect pancreatic and bile ductal cancers at their early stages by obtaining 3D OCT images of the tissue in questions and, in some cases collecting tissues for biopsy study. The collected 3D OCT images are then used for image-guided radiation therapy to treat pancreatic and bile ductal cancers at an early stage of the disease using, for example, internally and locally administered brachy radiation therapy (BRT).

In various embodiments, the invention provides systems and methods that integrate endoscopic three-dimensional high resolution optical coherence tomography (OCT) or ultrasound imaging devices with a high dose-rate (HDR) brachy therapy delivery mechanism in a compact and portable system to diagnose and treat early and late stage pancreatic and other intracavity types of cancers. The system can diagnose and precisely measure the location and size of the early or late stage pancreatic tumors (or other types of tumors) and treat them with an accurate, effective dose from inside the pancreas (or other related organs), thereby greatly reducing the radiation toxicity for the neighboring organs. The technique is low cost, less time consuming, and provides a reduced risk of side effects.

In one embodiment, the invention provides a catheter-based system for image-guided internally-administered treatment of medical conditions such as, for example, pancreatic cancer. A distal end of a catheter is positioned at a target site inside a patient's body. An imaging probe extended through the catheter collects image data of patient tissue at the target site. The image data is processed and a treatment plan is developed. A radiation source positioned at the distal end of the catheter without removing the catheter. In this way, images collected at the target tissue site can be used to develop a treatment plan and to guide the localized positioning and operation of a treatment device at the same internal tissue site—thereby providing higher resolution imaging (and thus more precise targeting) than external-based imaging modalities and reduced normal tissues exposure to radiation as compared to externally applied radiation therapies.

In some embodiments, the imaging probe is an OCT probe and a computer-based imaging and treatment planning system generates a three-dimensional model of the patient tissue based on the collected image data. In some embodiments, the radiation source is a HDR brachy radiation therapy probe.

In some embodiments, the proximal end of the catheter is fitted with a connector configured to selectively and interchangeably couple to a radiation therapy system and an OCT imaging system. In this way, once the catheter is placed at the target tissue site and the OCT image data is collected, the OCT imaging probe can be retracted and removed from the catheter while the catheter is left in place. The radiation source probe can then be extended through the catheter to the target tissue site at the distal end of the catheter and the proximal end of the catheter can be coupled to the radiation therapy system. In some embodiments, the connector includes a first threaded coupling with a first defined diameter for coupling to one of the OCT imaging system and the radiation therapy system and a second threaded coupling for coupling to the other one of the OCT imaging system and the radiation therapy system. The second threaded coupling has a second defined diameter that is less than the first defined diameter of the first threaded coupling and is positioned concentrically with the first threaded coupling, but at a linear distance from the first threaded coupling relative to the catheter length.

In some embodiments, the system is specifically adapted for early detection and treatment of specific types of cancers such as, for example, pancreatic cancer. However, in other embodiments, the system is adapted to use internal, locally collected image data to define a treatment plan and to apply local internal treatment for other specific disease or more general categories of treatments.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

In addition, it should be understood that embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software (e.g., stored on non-transitory computer-readable medium) executable by one or more processing units, such as a microprocessor and/or application specific integrated circuits ("ASICs"). As such, it should be noted that a plurality of hardware and software based devices, as well as a plurality of different structural components may be utilized to implement the invention. For example, "servers" and "computing devices" described in the specification can include one or more processing units, one or more computer-readable medium modules, one or more input/output interfaces, and various connections (e.g., a system bus) connecting the components.

Figure 1:
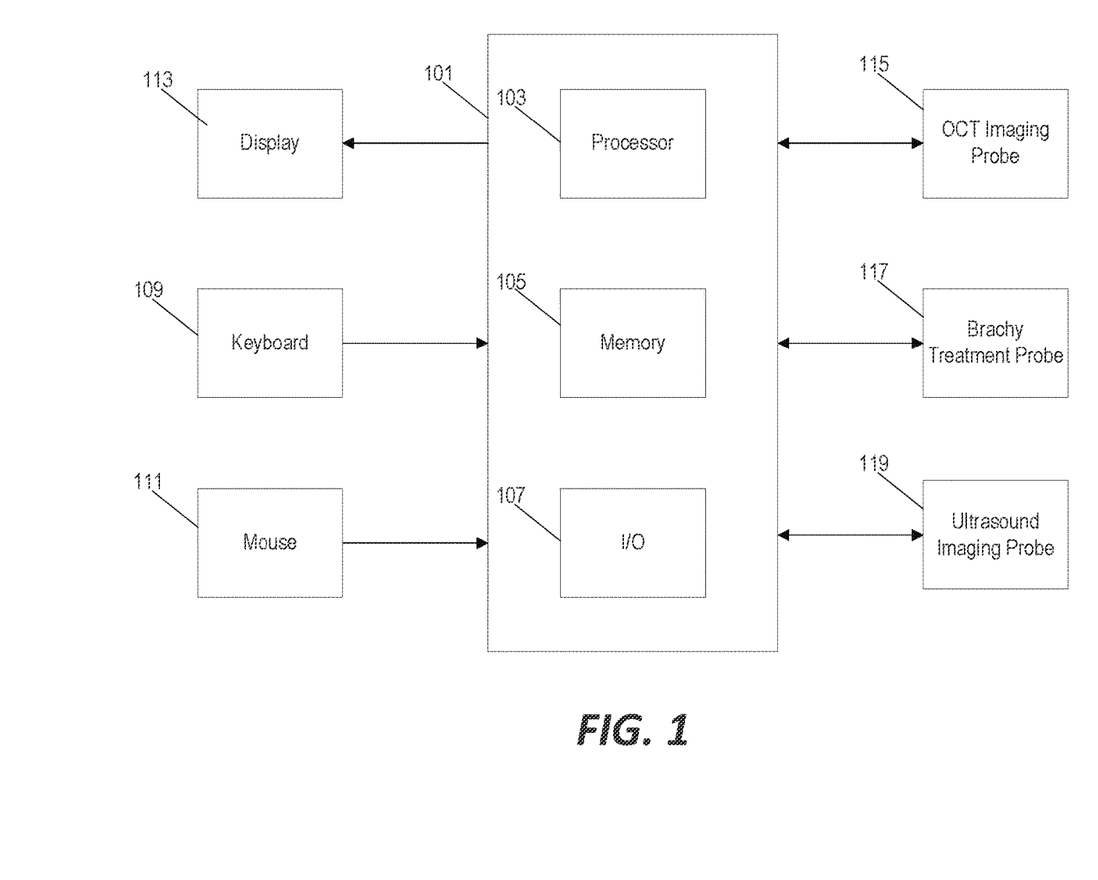
FIG. 1 is a block diagram of an endoscopic image-guided (OCT-guided or ultrasound-guided) HDR brachy radiation treatment system.

FIG. 1 illustrates a computer-based system 101 for image-guided, internal and localized treatment of pancreatic cancer.

The computer-based system 101 includes a processor 103 and a memory 105 storing instructions that are executed by the processor 103 to provide the system functionality described below. The memory 105 includes one or more non-transient computer readable memories such as, for example, a hard disk, Flash memory, or other types of RAM and ROM memory units. The processor 103 can include a variety of commercially available processing units including one or more of a microprocessor, microcontroller, PC computer processor, multiple core pipelined processors, or parallel processing system controllers.

The computer-based system 101 also includes an input/output interface module 107 that allows the computer-based system to communicate and interact with connected system components. For example, the computer-based system 101 receives user inputs from an operator interface—for example a connected keyboard 109 and mouse 111 as shown in FIG. 1—and provides a graphic user interface and various other viewable data to a display unit 113. The system 101 also interacts with an OCT imaging probe 115 to collect image data and recreate three-dimensional OCT images of internal patient tissue (as described further below). The system 101 is also coupleable to a HDR brachy treatment system including an endoscopic brachy treatment probe 117.

As discussed in further detail below, the endoscopic OCT probe 115 (or another imaging probe such as an ultrasound probe) is extended through a catheter tube that has been inserted into the pancreatic duct (or other intracavity pathway such as the esophagus, bronchi, etc.). The OCT probe 115 captures three-dimensional image data of the region of interest and returns the image data to the computer system 101 for processing and diagnosis. The computer system 101 then generates three-dimensional image models that are used to provide the exact location and size of a tumor. If the tumor is diagnosed as a cancer (this analysis may be combined with other diagnostic techniques such as pathology or biomarker) and needs to be treated with radiation therapy, an HDR brachy radiation treatment plan is developed by the computer-based system 101. The brachy treatment probe 117 is then inserted through the same catheter tube to the same location of the tumor and delivers a radiation dose to the tumor in accordance with the treatment plan. In some implementations, the entire process of generating the OCT images, diagnosing the tumor, developing the treatment plan, and delivering the radiation dose to the tumor is controlled automatically by a treatment console implemented by the computer-based system 101. In some implementations, the OCT imaging probe 115 is retracted and replaced with the brachy treatment probe manually.

Although the OCT imaging probe provides high-resolution imaging, it is less capable of providing image data deep below the surface. In some implementations, to see anatomical tissue structures more than 5 mm below the internal surface of the cavity, the endoscopic OCT imaging probe 115 is retracted from the catheter tube and replaced with an ultrasound imaging probe 119. As a result, the imaging system can be used to detect/diagnose and develop an image-guided treatment plan for smaller, early-stage tumors using the OCT probe and for larger, later-stage tumors using the ultrasound probe.

Figure 2:
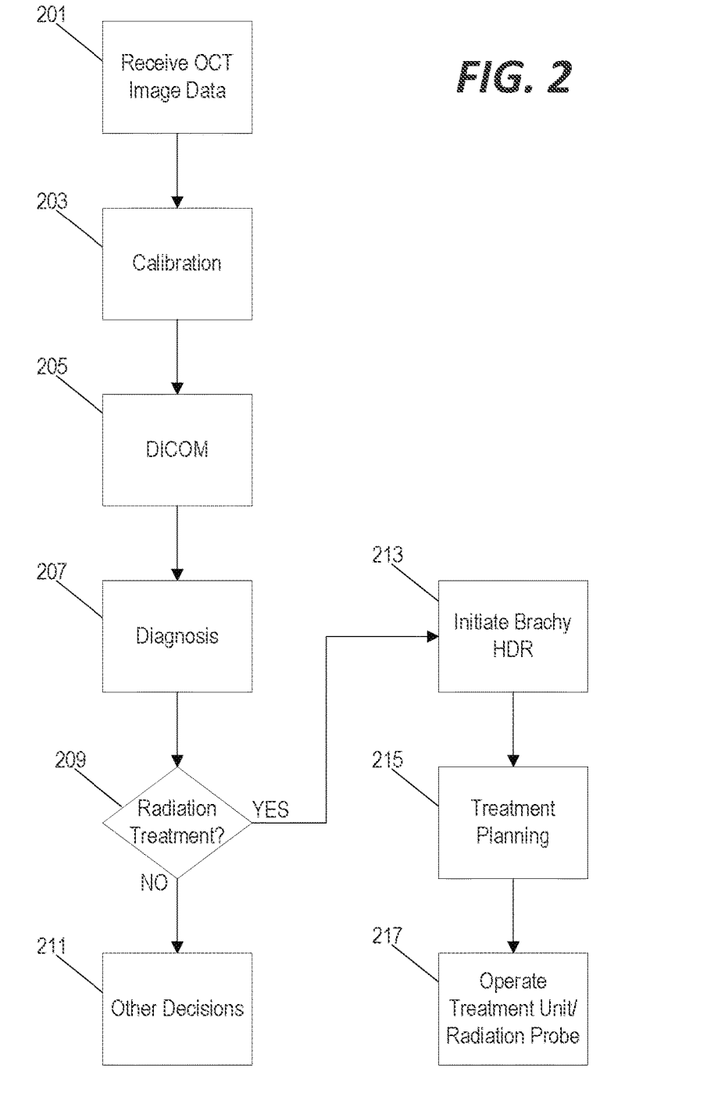
FIG. 2 is a flowchart of a method for performing HDR brachy radiation treatment using the system of FIG. 1 (OCT-guided).

FIG. 2 illustrates the schematic flow chart of the OCT-guided radiation therapy. OCT images are obtained by sending the OCT probe through the endoscopic catheter tube to the region of interest (ROI) area and capturing raw imaging data (step 201). The obtained raw imaging data is then transferred through an optical fiber connected to the probe to the computer 101 and is reconstructed to OCT images. The image system is calibrated (step 203) so that the OCT images have correct coordinate and scale for the objects scanned. The calibrated images are converted into Digital Imaging and Communications in Medicine (DICOM) format (step 205) and sent for diagnosis and treatment planning (step 207). The endoscopic OCT catheter tube used for imaging stays inside the patient and is to be used as a source guide tube for sending the radiation source probe through to the target ROI area (if necessary).

If the diagnosis (step 207) determines that no cancerous tumor is detected or otherwise determines that brachy radiation therapy would not be appropriate (step 209), then the system proceeds to assist the medical professional with other treatment and evaluation decisions (step 211). However, if radiation treatment is deemed to be appropriate, the image probe is retracted from the catheter tube and the radiation source probe is inserted to the ROI area (step 213). Because the position of the target has been identified in the images using the OCT image data, the treatment unit is configured to know exactly where to deliver the radiation and automatically develops a treatment plan accordingly (step 215). In some implementations, treatment planning systems such as the Varian Eclipse Treatment Planning system may be adapted to design an appropriate treatment plan based on the 3D OCT images. The treatment plan dictates how long the radiation source will be activate (i.e., the dosing) and how long it will remain at a given position. The system operates the radiation source probe according to the treatment plan to treat the cancerous tumor (step 217).

Figure 3A:
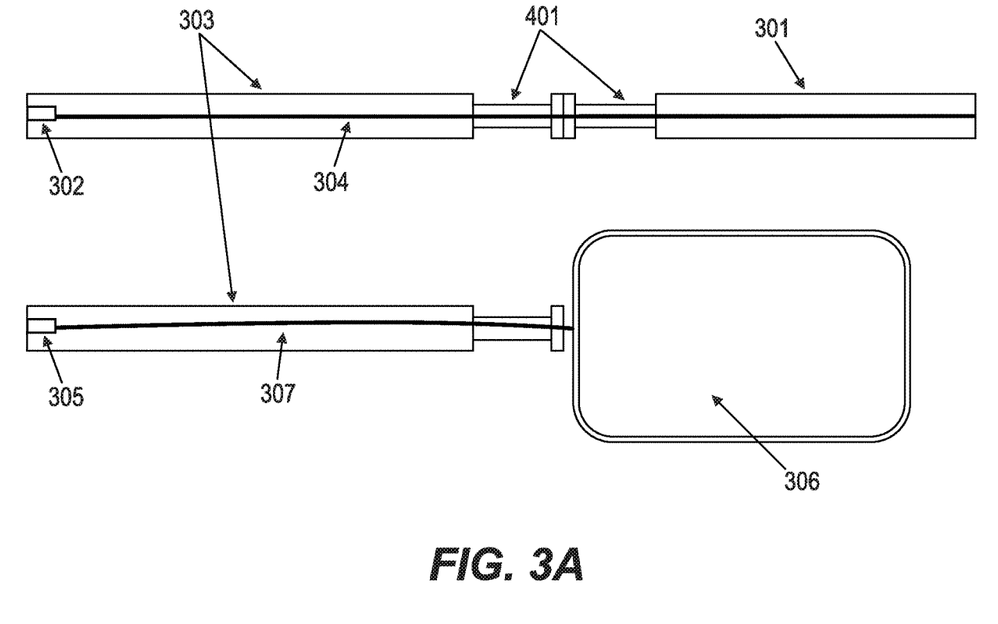
FIG. 3A is a partially transparent schematic view of a radiation source catheter coupled to an OCT catheter for OCT imaging and coupled to an HDR brachy treatment system for use with the system of FIG. 1.

FIG. 3A schematically illustrates a catheter connection mechanism for the performing both OCT imaging acquisition and radiation treatment. A radiation source catheter 303 is typically of a defined length; however, to provide additional flexibility during imaging, the radiation source catheter 303 is coupled to an OCT catheter 301 by a connector mechanism 401. The details of the connector mechanism 401 are discussed further below. To perform OCT imaging, the source catheter 303 is coupled to the OCT catheter 301 by the coupling mechanism and the OCT probe 302 is inserted through the coupled catheters to the distal end of the source catheter 303 as shown in the top schematic of FIG. 3A. An optic cable 304 couples the OCT probe 302 to an OCT control and processing machine external to the patient. The catheter lengths illustrated in FIG. 3A are not drawn to scale and in some implementations the source catheter 303 is sized so that the distal end of the source catheter 303 can reach the target site while the connector 401 and the entire OCT catheter 301 remain external to the patient.

After OCT imaging is completed, the OCT probe 302 is removed and the OCT catheter 301 is disconnected from the source catheter 303. As shown in the lower schematic of FIG. 3A, a radiation source probe 305 is inserted through the source catheter 303 to the distal end of the source catheter 303 and the source catheter 303 is coupled to the radiation source control system 306. A source wire 307 runs through the source catheter 303 and couples the source probe 305 to the radiation source control system 306.

Figure 3B:
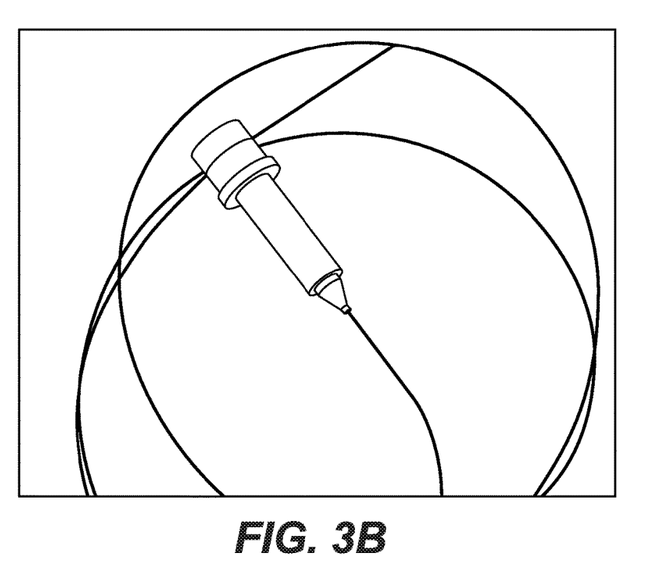
FIG. 3B is an overhead view of a proximal end of the catheter of FIG. 3A.
Figure 3C:
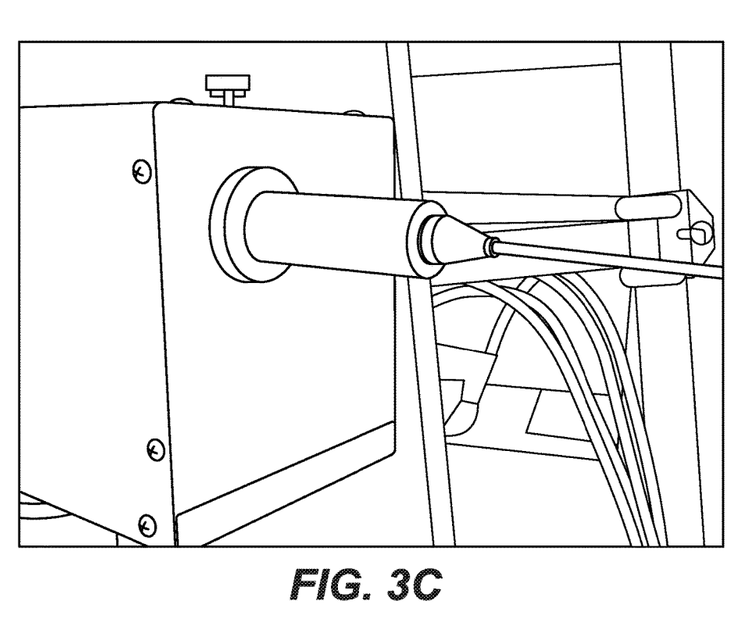
FIG. 3C is a perspective view of a table-top, software controller pull-back system for use with the endoscopic OCT catheter probe of FIG. 3A

FIG. 3B illustrates the catheter 303 in further detail including the connector mechanism 401 on the proximal end of the catheter that is used to couple the OCT catheter to the OCT imaging system. The OCT catheter probe 302 travels through the catheter tube to the region of interest and scans 360° to capture image data. The 3D image data can be obtained by moving the probe on a certain step size at different axial positions using a pull-back system such as the one illustrated in FIG. 3C. The pull-back system of FIG. 3C is a computerized, software-controlled automated table-top system that accurately and reliably controls the movement of the OCT probe. The probe is connected by an optic fiber to a computer which reconstructs the raw image data from the OCT probe 302 include three-dimensional OCT images.

Figure 3D:
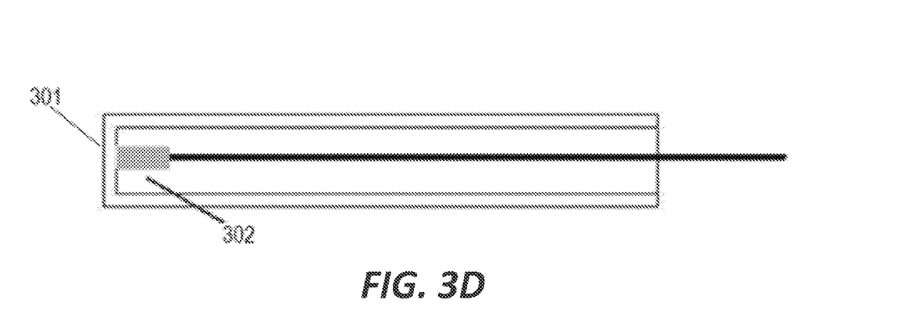
FIG. 3D is a partially transparent schematic view of another example of an OCT catheter with an OCT imaging probe positioned for use with the system of FIG. 1.
Figure 3E:
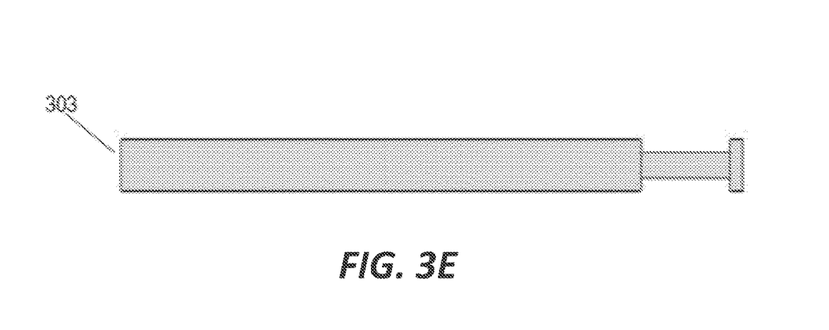
FIG. 3E is a partially transparent schematic view of a radiation source catheter for use with the OCT catheter of FIG. 3D.
Figure 3F:
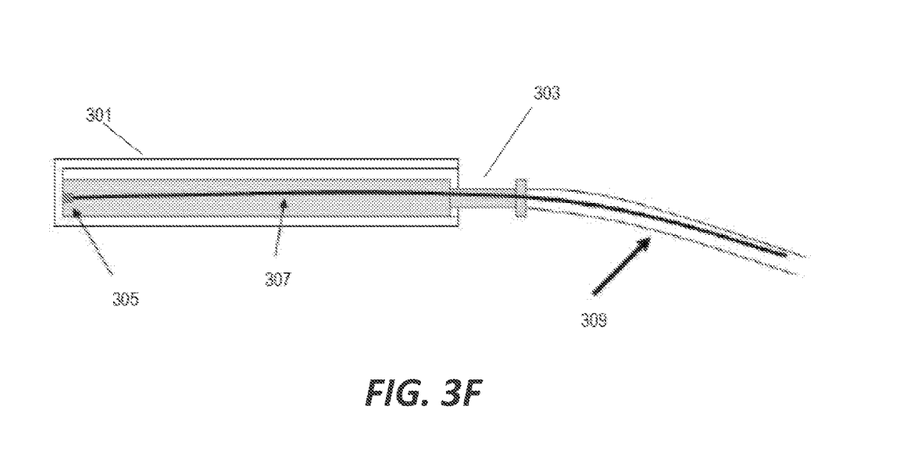
FIG. 3F is a partially transparent schematic view of the radiation source catheter of FIG. 3E positioned within the OCT catheter of FIG. 3D for positioning a radiation source probe at a target site for HDR brachy treatment.

FIGS. 3D-3F schematically illustrate an alternative configuration for the catheter/probe system used in the system of FIG. 1. As shown in FIG. 3D, the transparent catheter tube 301 with an OCT imaging probe 302 inserted and positioned at a distal end of the catheter tube 301. The radiation source catheter 303, as shown in FIG. 3E, is sized to have a slightly smaller diameter than the OCT catheter tube 301. Therefore, as illustrated in FIG. 3F, after the OCT imaging probe 302 is retracted and removed from the OCT catheter tube 301, the radiation source catheter 303 can be extended through the OCT catheter tube 301 and positioned at the target ROI area. When configured for delivery of radiation therapy, the radiation source 305 is positioned at the distal end of the source catheter 303 and is coupled to an HDR brachy treatment machine by a source wire 307. A source guide tube 309 also extends through the OCT catheter tube 301 to couple the source wire 307 to the treatment machine.

Figure 4:
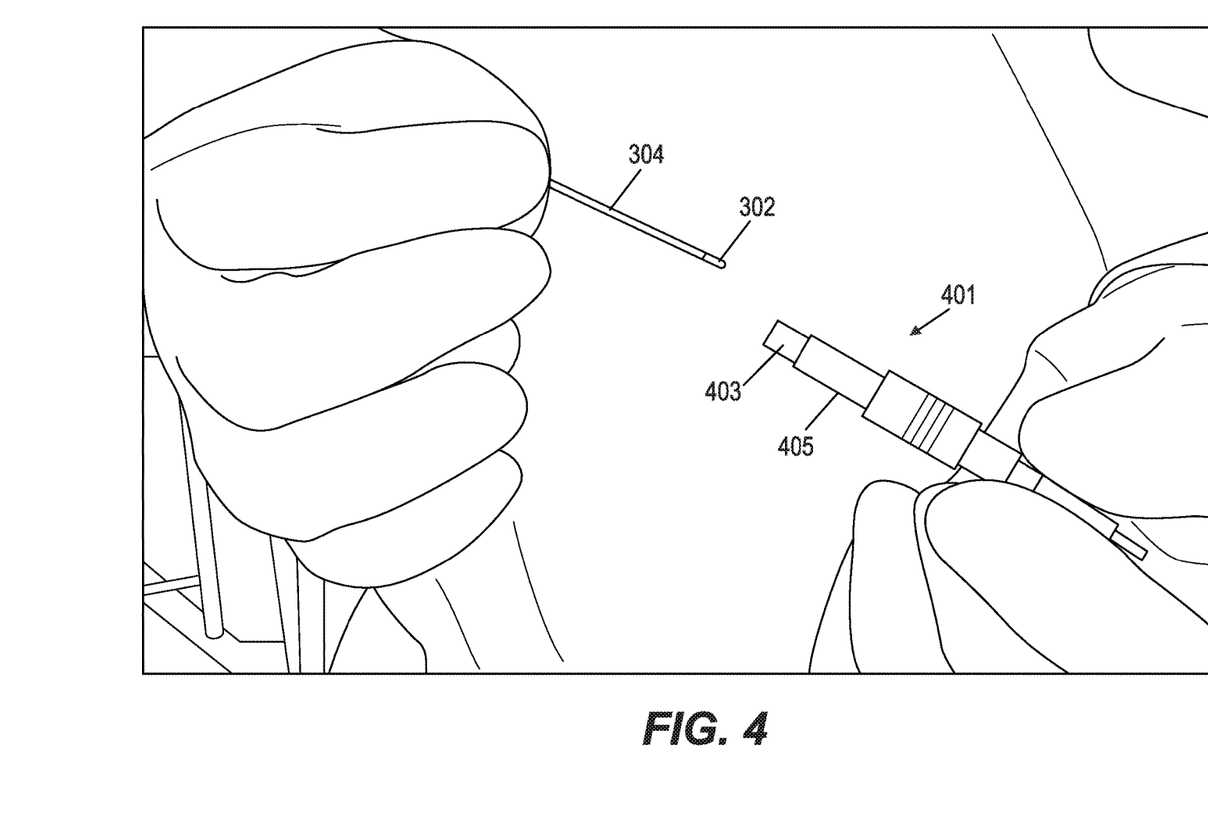
FIG. 4 is a perspective view of a proximal end connector for the combination OCT/radiation source catheter assembly of FIG. 3C.

FIG. 4 illustrates a connection mechanism 401 that is attached to the proximal end of the OCT catheter tube 302 and is used to couple the catheter—and, thereby, the OCT probe or the radiation source probe—to the radiation treatment machine or the imaging computer system. The connector 401 includes a first threaded coupling 403 that is sized to couple to either the radiation machine or the OCT imaging system. A second threaded coupling 405 is positioned concentric with the first threaded coupling 403 and at a linear distance from the first threaded coupling 403 relative to the catheter tube. The catheter tube is coupled to the connector 401 at the end opposite the first threaded coupling 403. A hollow central bore is provided through the connector 401 such that the OCT probe 302 and the OCT optic wire 304 can be inserted through the hollow bore until the OCT probe 302 reaches the target ROI. The radiation source probe can be similarly inserted through the hollow central bore when the OCT probe is replaced with the source probe.

The optic fiber of the imaging system and the delivery of potential damaging radiation from the treatment machine both require a secure coupling. The use of two separate threaded couplings provided by the connector 401 provides the necessary secure coupling and the versatility necessary to replace the OCT imaging probe with an HDR brachy treatment probe without removing or replacing the catheter. As a result, the system is capable of capturing image data, using the image data to develop a treatment plan, and delivering radiation treatment to the same target ROI. Furthermore, because the flexible OCT catheter tube moves with the patient, shifting of the patient's body during the diagnosis and treatment procedures does not cause adversely affect the reliability of the application of radiation therapy. The distal end of the catheter remains at the same location while image data is collected, while the OCT probe is removed, during image diagnosis, and while radiation is applied.

Furthermore, although the examples of FIGS. 3A-4 utilize a catheter system in which the OCT probe is removed before the radiation source probe is inserted, in some implementations, the catheter tube is adapted to accommodate both the OCT probe and the radiation source probe. Such implementations may include, for example, a dual channel catheter tube or single channel tube with a distal end that is specifically configured to securely and safely hold the OCT probe and the radiation source probe in proper positions relative to each other.

Figure 5A:
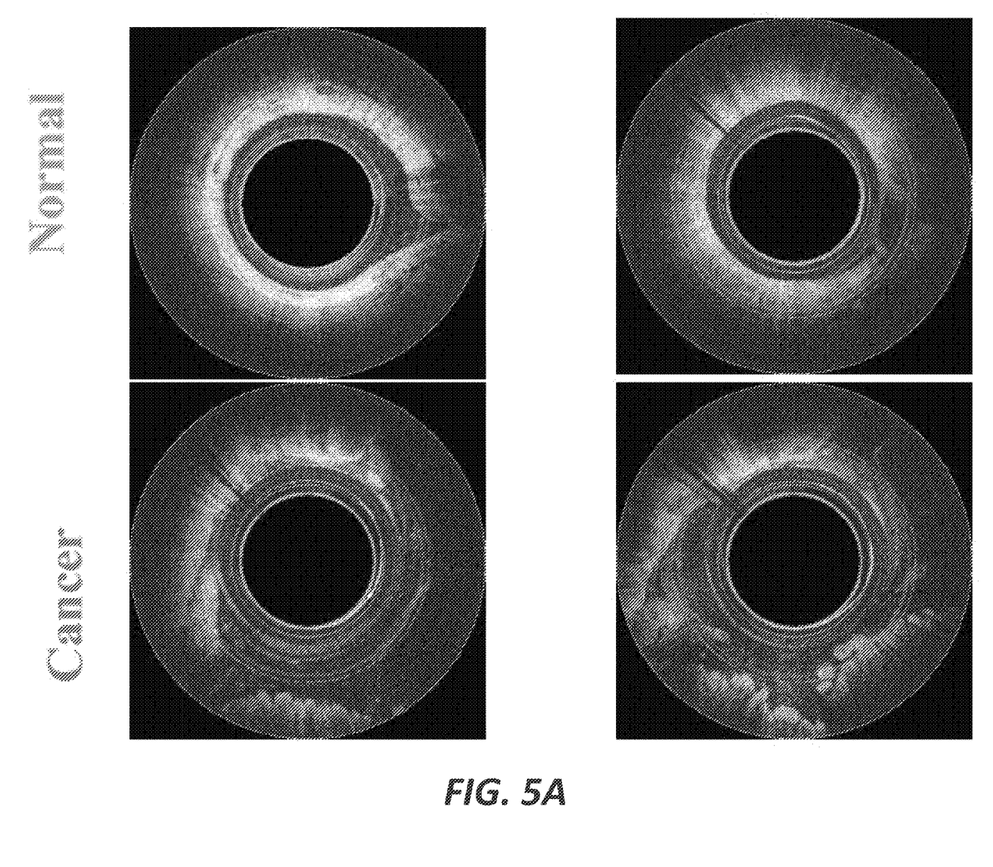
FIG. 5A is a series of OCT-generated 2-D images illustrating the difference between normal pancreatic tissue and cancerous tissue.
Figure 5B:
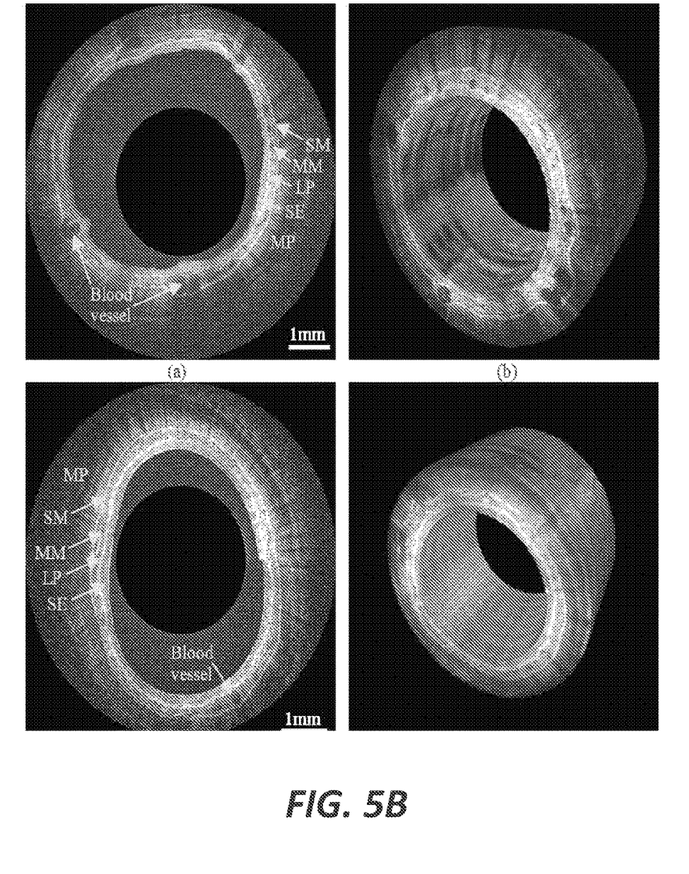
FIG. 5B is a series of OCT-generated 3-D images of an anatomical structure.

FIG. 5A provides an example of OCT images captured by the OCT image probe in the systems described above. The top two images show normal tissue while the lower two images show abnormal, cancerous tissue. As illustrates by the examples of FIG. 5A, the OCT image data provide sufficient resolution to detect and diagnose cancerous tumors at an early stage. However, for later-stage, larger tumors, OCT images can be fused with supplemental image data from CT, MM, or endoscopic ultrasound to more completely characterize the position, shape, and size of the cancerous growth. FIG. 5B illustrates an example of a three-dimensional OCT image reconstruction of esophageal tissue that can be similarly used to detect and diagnose cancerous tumors.

Figure 6:
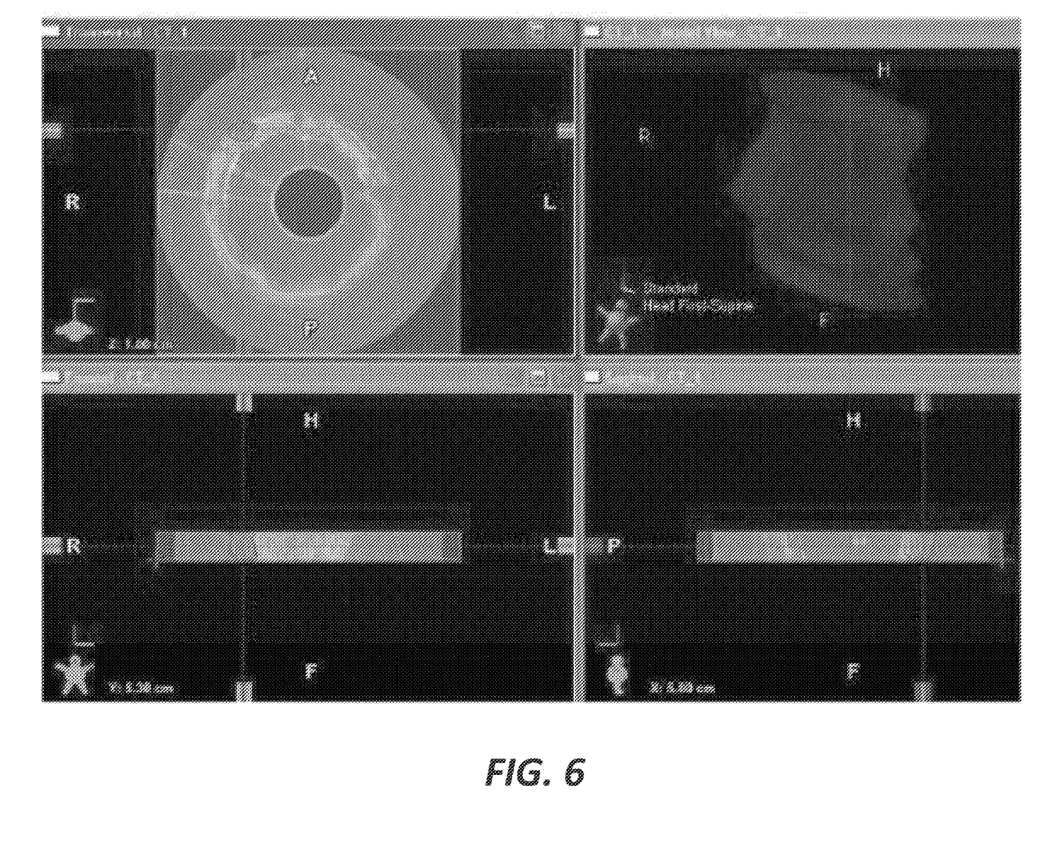
FIG. 6 is a screen-shot of a treatment planning interface using OCT image guidance for the system of FIG. 1.

FIG. 6 illustrates an example of a graphical user interface that may be displayed to the medical professional during the diagnosis stages. The upper left image shows transverse cross section of the OCT image data. The lower left image shows the frontal cross section and the lower right image shows the sagittal cross section. In each of those three cross-sections, a cancerous tumor is outlined in red. The upper right image shows a three-dimensional reconstruction of the contours and delineation of the region of interest.

Figure 7:
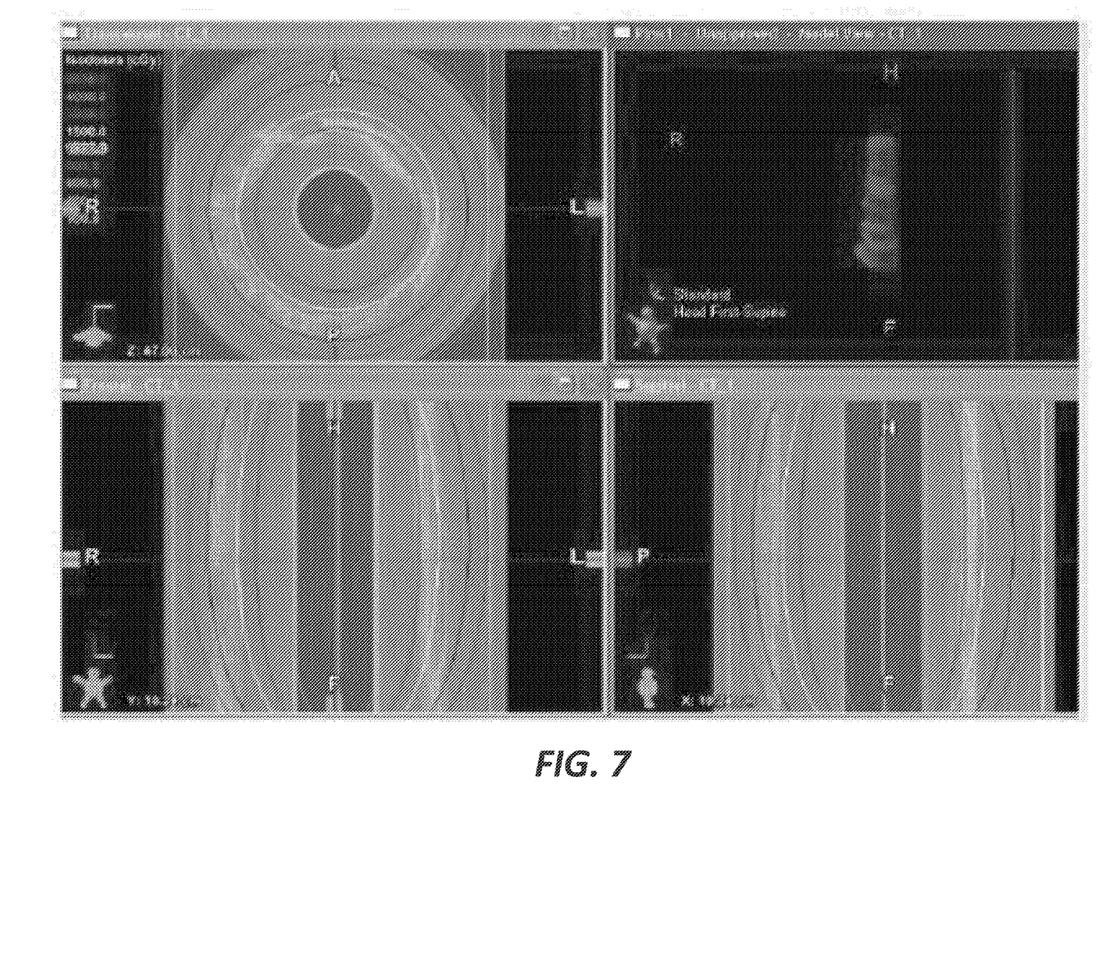
FIG. 7 is a screen-shot of a treatment plan and dose distribution interface for the system of FIG. 1.

FIG. 7 illustrates an example of a graphical user interface that may be displayed to the medical professional while developing a proper treatment plan. Again, the upper left image is a transverse cross-sectional image of the ROI, the lower left image is a frontal cross-section, and the lower right image is a sagittal cross-section. The upper right shows the three-dimensional model reconstruction of the region of interest. The colored lines illustrate the radiation dosing (i.e., intensity and duration) for a treatment plan based on the OCT images of FIG. 6 after a target tumor has been identified and characterized.

As discussed above, the OCT imaging modality is applied endoscopically to generate high-resolution image data which uniquely enables the system to detect and diagnose early-stage cancerous tumors in soft tissue such as, for example, pancreatic tumors. Furthermore, because the radiation dosing is provided at the same target location, through the same catheter, and according to a treatment plan developed based on the high-resolution OCT images, radiation therapy can be directly target to the cancerous tumors results in significantly reduce radiation exposure to other nearby tissues.

Figure 8:
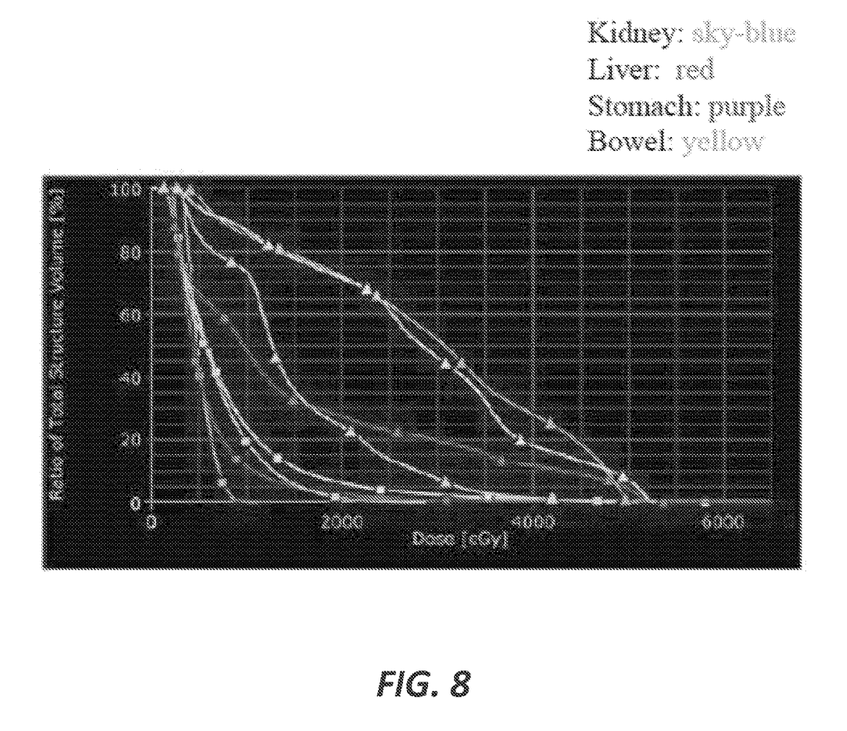
FIG. 8 is a graph of relative levels of radiation exposure for various organs using the system of FIG. 1 as compared to levels of radiation exposure using externally applied radiation treatment.

FIG. 8 shows a comparison of the dose volume histograms (DVH) for external beam radiation therapy (EBRT; represented by the triangle notations) and endoscopic brachy radiation therapy (represented by the square notations) for organs at risk of inadvertent radiation exposure during radiation treatment of the pancreas. The illustrated organs include the kidney (blue), the liver (red), the stomach (purple), and the bowel (yellow). As demonstrated by the graph of FIG. 8, these organs receive significantly lower doses of radiation using the methods and systems described above as compared with EBRT while the pancreatic tumor still receives the prescribed dose.

Figure 9A:
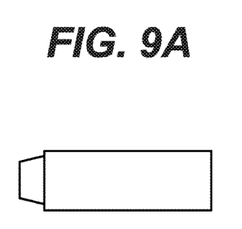
FIG. 9A is a side view of a phantom device for confirming imaging function of the OCT device of the system of FIG. 1 prior to insertion.
Figure 9B:
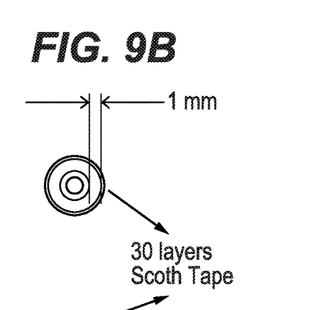
FIG. 9B is a rear view of the phantom device of FIG. 9A.
Figure 9C:
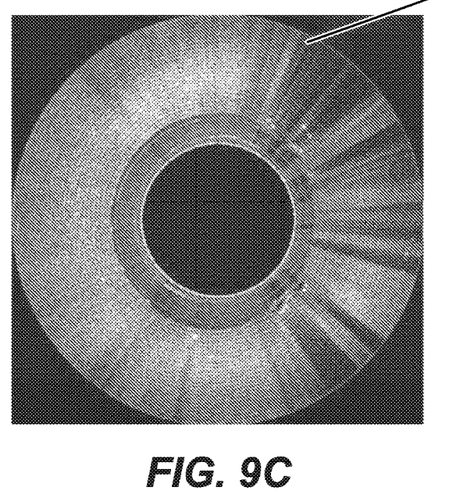
FIG. 9C is an image captured by the OCT probe of FIG. 1 when inserted into the phantom device of FIG. 9A.

FIGS. 9A and 9B illustrate a phantom device that can be used prior to inserting the catheter to confirm that the imaging function of the OCT probe is operational and, in some implementations, to verify that other functional aspects of the system are operational. The phantom device is a cylindrical device with a hollow channel extending through its center. In the example illustrated in FIGS. 9A and 9B, the phantom device is constructed by wrapping 30 layers of Scotch tape to form a tube with a 1 mm thickness. FIG. 9C illustrates and example of image data collected by an OCT probe inserted into the phantom. The image data of FIG. 9C confirms that the OCT probe is functioning before the OCT probe is inserted into the patient's anatomy. In some implementations, the phantom device is designed to be tissue-equivalent and can be used routinely to check and calibrate the system on every aspect from diagnosis and treatment including imaging quality, image scale factor, precision of position detection, the dose delivery accuracy Thus, the invention provides, among other things, a system and method for high-resolution and high-accuracy image-guided endoscopic radiation treatment of cancers with reduced risk of radiation exposure to nearby tissues. Various features and advantages of the invention are set forth in the following claims.

What is claimed is:

1. A method of treating intracavity tissue, the method comprising:
    coupling a distal end of an imaging probe catheter to a proximal end of the catheter tube, the imaging probe catheter partially containing the imaging probe;
    positioning a distal end of a catheter tube at a target site inside an anatomical cavity;
    operating an imaging probe positioned at the distal end of the catheter tube to capture image data of the target site;
    generating three-dimensional images of the target site based on the captured image data;
    developing a radiation treatment plan based on the three-dimensional images;
    decoupling the distal end of the imaging probe catheter from the proximal end of the catheter tube before retracting the imaging probe from the catheter tube;
    retracting the imaging probe from the catheter tube after capturing the image data of the target site while the distal end of the catheter tube remains positioned at the target site;
    inserting the radiation source probe through the catheter tube to position the radiation source probe at the distal end of the catheter tube after retracting the imaging probe and before delivering a dosage of radiation;
    coupling a radiation controller to the proximal end of the catheter tube after inserting the radiation probe into the catheter tube; and
    operating a radiation source probe to deliver the dosage of radiation according to the radiation treatment plan, wherein the radiation source probe is operated while positioned at the distal end of the catheter tube at the target site and, wherein the catheter tube is not retracted after capturing the image data and before delivering the dosage of radiation,
    wherein the proximal end of the catheter tube includes a first threaded coupling and a second threaded coupling, wherein the second threaded coupling is positioned coaxial to the first threaded coupling at a linear distance from the first coupling, and wherein a diameter of the first threaded coupling is different from a diameter of the second threaded coupling,
    wherein coupling a distal end of the imaging probe catheter to a proximal end of the catheter tube includes coupling the distal end of the imaging probe catheter to the first threaded coupling of the catheter tube, and
    wherein coupling the radiation controller to the proximal end of the catheter tube includes coupling the radiation controller to the second threaded coupling of the catheter tube.

2. The method of claim 1, wherein the act of operating the imaging probe to capture image data includes operating an optical coherence tomography (OCT) imaging probe to capture three-dimensional optical coherence tomography (OCT) image data of tissue at the target site.

3. The method of claim 1, wherein the act of operating the imaging probe to capture image data includes operating an ultrasound imaging probe to capture ultrasound image data of tissue at the target site.

4. The method of claim 1, wherein the act of operating the radiation source probe to deliver a dosage of radiation includes operating a radiation source probe to deliver high dose-rate (HDR) brachy radiation therapy.

5. The method of claim 1, wherein the act of operating the imaging probe to capture image data includes operating an optical coherence tomography (OCT) imaging probe to capture three-dimensional optical coherence tomography (OCT) image data of tissue at the target site, and further comprising:
    inserting an ultrasound imaging probe through the catheter tube to position the ultrasound imaging probe at the distal end of the catheter tube after retracting the optical coherence tomography (OCT) imaging probe;
    operating the ultrasound imaging probe while positioned at the distal end of the catheter tube to capture ultrasound image data of the target site; and
    retracting the ultrasound imaging probe from the catheter tube after capturing the ultrasound image data of the target site, wherein the radiation source probe is inserted through the catheter tube after the ultrasound imaging probe is retracted.

6. The method of claim 1, wherein the distal end of the imaging probe is coupled to the proximal end of the catheter tube at a location external to an imaging subject.

7. The method of claim 1, wherein inserting the radiation source probe through the catheter tube includes inserting a radiation source probe catheter into the catheter tube until a distal end of the radiation source probe catheter is positioned at the distal end of the catheter tube, the radiation source probe catheter enclosing the radiation source probe.

8. The method of claim 1, wherein developing the radiation treatment plan based on the three-dimensional images includes determining an appropriate radiation treatment plan based on the captured image data while the distal end of the catheter tube remains positioned at the target site.

9. The method of claim 1, further comprising operating a controlled mechanical pull-back system to retract the imaging probe at defined step intervals while operating the imaging probe to capture the image data.

10. A method of treating intracavity tissue, the method comprising:
    positioning a distal end of a catheter tube at a target site inside an anatomical cavity;
    operating an imaging probe positioned at the distal end of the catheter tube to capture image data of the target site;
    generating three-dimensional images of the target site based on the captured image data;
    developing a radiation treatment plan based on the three-dimensional images; and
    operating a radiation source probe to deliver a dosage of radiation according to the radiation treatment plan, wherein the radiation source probe is operated while positioned at the distal end of the catheter tube at the target site and, wherein the catheter tube is not retracted after capturing the image data and before delivering the dosage of radiation, and
    further comprising calibrating the imaging probe by positioning the distal end of the catheter tube into a tissue-equivalent phantom, wherein the tissue-equivalent phantom includes a hollow tube with a thickness of approximately 1 mm.

11. The method of claim 10, wherein calibrating the imaging probe includes evaluating at least one variable selected from a group consisting of imaging quality, image scale factor, precision of position detection, and dose delivery accuracy.

* * * * *